(12) United States Patent
Mohan et al.

(10) Patent No.: US 9,867,733 B2
(45) Date of Patent: Jan. 16, 2018

(54) TISSUE ADJUSTMENT IMPLANT (71) Applicants: Cook Medical Technologies LLC, Bloomington, IN (US); Cook Biotech Incorporated, West Lafayette, IN (US)

(72) Inventors: P. Arun Mohan, West Lafayette, IN (US); Christine Bronikowski, Lafayette, IN (US); Ryan Bernstein, Lafayette, IN (US); Joseph Obermiller, West Lafayette, IN (US); Patrick C. Melder, Marietta, GA (US)

(73) Assignees: COOK MEDICAL TECHNOLOGIES LLC, Bloomington, IN (US); COOK BIOTECH INCORPORATED, West Lafayette, IN (US)

( * ) Notice: Subject to any disclaimer, the term of this patent is extended or adjusted under 35 U.S.C. 154(b) by 554 days.

(21) Appl. No.: 14/449,195

(22) Filed: Aug. 1, 2014

(65) Prior Publication Data
US 2015/0034095 A1 Feb. 5, 2015

Related U.S. Application Data (60) Provisional application No. 61/861,089, filed on Aug. 1, 2013.

(51) Int. Cl.
*A61F 5/56* (2006.01)
(52) U.S. Cl.
CPC ............... *A61F 5/56* (2013.01); *A61F 5/566* (2013.01); *A61F 2005/563* (2013.01)

(58) Field of Classification Search
CPC ....... A61F 5/56; A61F 5/566; A61F 2005/563
See application file for complete search history.

(56) References Cited

U.S. PATENT DOCUMENTS

| 4,024,859 A | 5/1977 | Slepyan et al. |
| 4,064,873 A | 12/1977 | Swenson |
| 4,608,972 A | 9/1986 | Small |
| 4,917,604 A | 4/1990 | Small |
| 5,674,191 A | 10/1997 | Edwards et al. |
| 5,988,171 A | 11/1999 | Sohn et al. |

(Continued)

FOREIGN PATENT DOCUMENTS

| WO | WO 0145765 A1 * | 6/2001 | ............. A61K 35/22 |
| WO | 2007149469 | 12/2007 | |

(Continued)

OTHER PUBLICATIONS

International Searching Authority, International Search Report and Written Opinion for International application No. PCT/US2014/049341, dated Nov. 19, 2014, pp. 1-11.

(Continued)

*Primary Examiner* — Tarla Patel
(74) *Attorney, Agent, or Firm* — Buchanan Van Tuinen LLC (57) ABSTRACT

Tissue adjustment implants useful for adjusting a position of tissue in a patient are described. In an embodiment, a tissue adjustment implant includes a main body having a series of outwardly-extending projections. The tissue adjustment implants can be used in a variety of treatments, such as in the treatment of Obstructive Sleep Apnea and snoring.

20 Claims, 7 Drawing Sheets

(56) References Cited

U.S. PATENT DOCUMENTS

| | | | |
|---|---|---|---|
| 6,159,208 A | 12/2000 | Hovda et al. | |
| 6,161,541 A | 12/2000 | Woodson | |
| 6,397,841 B1 | 6/2002 | Kenyon et al. | |
| 6,408,851 B1 | 6/2002 | Karell | |
| 6,513,530 B2 | 2/2003 | Knudson et al. | |
| 6,513,531 B2 | 2/2003 | Knudson et al. | |
| 6,523,541 B2 | 2/2003 | Knudson et al. | |
| 6,895,963 B1 | 5/2005 | Martin et al. | |
| 6,910,483 B2 | 6/2005 | Daly et al. | |
| 6,955,172 B2 | 10/2005 | Nelson et al. | |
| 6,974,419 B1 | 12/2005 | Voss et al. | |
| 7,004,941 B2 | 2/2006 | Tvinnereim et al. | |
| 7,047,979 B2 | 5/2006 | Conrad et al. | |
| 7,063,089 B2 | 6/2006 | Knudson et al. | |
| 7,073,505 B2 | 7/2006 | Nelson et al. | |
| 7,090,672 B2 | 8/2006 | Underwood et al. | |
| 7,128,069 B2 | 10/2006 | Farrugia et al. | |
| 7,168,429 B2 | 1/2007 | Matthews et al. | |
| 7,188,627 B2 | 3/2007 | Nelson et al. | |
| 7,213,599 B2 | 5/2007 | Conrad et al. | |
| 7,216,647 B2 | 5/2007 | Lang et al. | |
| 7,255,109 B2 | 8/2007 | Knudson et al. | |
| 7,291,112 B2 | 11/2007 | Martin et al. | |
| 7,337,778 B2 | 3/2008 | Martin et al. | |
| 7,337,781 B2 | 3/2008 | Vassallo | |
| 7,360,542 B2 | 4/2008 | Nelson et al. | |
| 7,363,926 B2 | 4/2008 | Pflueger et al. | |
| 7,387,634 B2 | 6/2008 | Benderev | |
| 7,401,611 B2 | 7/2008 | Conrad et al. | |
| 7,491,200 B2 | 2/2009 | Underwood | |
| 7,607,439 B2 | 10/2009 | Li | |
| 7,644,714 B2 | 1/2010 | Atkinson et al. | |
| 7,658,192 B2 | 2/2010 | Harrington | |
| 7,669,603 B2 | 3/2010 | Knudson et al. | |
| 7,673,635 B2 | 3/2010 | Conrad et al. | |
| 7,680,538 B2 | 3/2010 | Durand et al. | |
| 7,703,460 B2 | 4/2010 | Conrad et al. | |
| 7,813,812 B2 | 10/2010 | Kieval et al. | |
| 7,827,038 B2 | 11/2010 | Richard et al. | |
| 7,827,988 B2 | 11/2010 | Matthews et al. | |
| 7,845,357 B2 | 12/2010 | Buscemi et al. | |
| 7,856,980 B2 | 12/2010 | Lang et al. | |
| 7,874,291 B2 | 1/2011 | Ging et al. | |
| 7,884,101 B2 | 2/2011 | Teegarden et al. | |
| 7,909,037 B2 | 3/2011 | Hegde et al. | |
| 7,909,038 B2 | 3/2011 | Hegde et al. | |
| 7,921,850 B2 | 4/2011 | Nelson et al. | |
| 7,934,506 B2 | 5/2011 | Woodson et al. | |
| 7,935,065 B2 | 5/2011 | Martin et al. | |
| 7,938,114 B2 | 5/2011 | Matthews et al. | |
| 7,949,400 B2 | 5/2011 | Kieval et al. | |
| 7,954,494 B1 | 6/2011 | Connor | |
| 7,955,267 B2 | 6/2011 | Voss et al. | |
| 7,959,554 B2 | 6/2011 | McAlexander et al. | |
| 7,975,700 B2 | 7/2011 | Frazier et al. | |
| 7,976,471 B2 | 7/2011 | Martin et al. | |
| 7,980,248 B2 | 7/2011 | Hegde et al. | |
| 7,992,564 B2 | 8/2011 | Doshi et al. | |
| 7,992,566 B2 | 8/2011 | Pflueger et al. | |
| 7,992,567 B2 | 8/2011 | Hirotsuka et al. | |
| 7,997,266 B2 | 8/2011 | Frazier et al. | |
| 7,997,267 B2 | 8/2011 | Ging et al. | |
| 8,020,560 B2 | 9/2011 | Paraschac et al. | |
| 8,074,655 B2 | 12/2011 | Sanders | |
| 8,096,303 B2 | 1/2012 | Dineen et al. | |
| 8,167,787 B2 | 5/2012 | Gillis | |
| 8,186,355 B2 | 5/2012 | van der Burg et al. | |
| 8,220,466 B2 | 7/2012 | Frazier et al. | |
| 8,220,467 B2 | 7/2012 | Sanders | |
| 8,327,854 B2 | 12/2012 | Gillis et al. | |
| 8,460,322 B2 | 6/2013 | van der Burg et al. | |
| 8,932,325 B2 * | 1/2015 | Stanley | A61B 17/0057 606/213 |
| 8,936,616 B2 | 1/2015 | Nelson | |
| 2001/0050085 A1 | 12/2001 | Knudson et al. | |
| 2003/0111079 A1 | 6/2003 | Matthews et al. | |
| 2003/0140925 A1 | 7/2003 | Sapienza et al. | |
| 2003/0168064 A1 | 9/2003 | Daly et al. | |
| 2004/0028676 A1 | 2/2004 | Klein et al. | |
| 2004/0112387 A1 | 6/2004 | Lang et al. | |
| 2004/0153127 A1 | 8/2004 | Gordon et al. | |
| 2004/0187870 A1 | 9/2004 | Matthews et al. | |
| 2005/0005937 A1 | 1/2005 | Farrugia et al. | |
| 2005/0098184 A1 | 5/2005 | Conrad et al. | |
| 2005/0103339 A1 | 5/2005 | Daly et al. | |
| 2005/0126563 A1 | 6/2005 | van der Burg et al. | |
| 2005/0178384 A1 | 8/2005 | Martin et al. | |
| 2005/0217673 A1 | 10/2005 | Daly et al. | |
| 2005/0267547 A1 | 12/2005 | Knudson et al. | |
| 2005/0279365 A1 | 12/2005 | Armijo et al. | |
| 2006/0000475 A1 | 1/2006 | Matthews et al. | |
| 2006/0070626 A1 | 4/2006 | Frazier et al. | |
| 2006/0150986 A1 | 7/2006 | Roue et al. | |
| 2006/0207612 A1 | 9/2006 | Jackson et al. | |
| 2006/0235877 A1 | 10/2006 | Richard et al. | |
| 2007/0132117 A1 | 6/2007 | Truitt et al. | |
| 2007/0134085 A1 | 6/2007 | Daly et al. | |
| 2007/0144539 A1 | 6/2007 | van der Burg et al. | |
| 2007/0157928 A1 | 7/2007 | Pujol et al. | |
| 2007/0157934 A1 | 7/2007 | Lang et al. | |
| 2007/0207994 A1 | 9/2007 | Teegarden et al. | |
| 2007/0209664 A1 | 9/2007 | Paraschac et al. | |
| 2007/0209665 A1 | 9/2007 | Gillis et al. | |
| 2007/0244086 A1 | 10/2007 | Teegarden et al. | |
| 2007/0256693 A1 | 11/2007 | Paraschac et al. | |
| 2007/0287923 A1 | 12/2007 | Adkins et al. | |
| 2008/0023012 A1 | 1/2008 | Dineen et al. | |
| 2008/0027560 A1 | 1/2008 | Jackson et al. | |
| 2008/0041382 A1 | 2/2008 | Matthews et al. | |
| 2008/0041383 A1 | 2/2008 | Matthews et al. | |
| 2008/0045813 A1 | 2/2008 | Phuah et al. | |
| 2008/0053461 A1 | 3/2008 | Hirotsuka et al. | |
| 2008/0058584 A1 | 3/2008 | Hirotsuka et al. | |
| 2008/0066753 A1 | 3/2008 | Martin et al. | |
| 2008/0066765 A1 | 3/2008 | Paraschac et al. | |
| 2008/0066769 A1 | 3/2008 | Dineen et al. | |
| 2008/0097380 A1 | 4/2008 | Li | |
| 2008/0099019 A1 | 5/2008 | Martin et al. | |
| 2008/0194953 A1 | 8/2008 | Kerber | |
| 2008/0208265 A1 | 8/2008 | Frazier et al. | |
| 2008/0251071 A1 | 10/2008 | Armitstead et al. | |
| 2009/0044814 A1 | 2/2009 | Iancea et al. | |
| 2009/0053306 A1 | 2/2009 | Agarwal et al. | |
| 2009/0060905 A1 | 3/2009 | Martin et al. | |
| 2009/0099471 A1 | 4/2009 | Broadley et al. | |
| 2009/0131923 A1 | 5/2009 | Connors et al. | |
| 2010/0004264 A1 | 1/2010 | Xiong et al. | |
| 2010/0010061 A1 | 1/2010 | Cooper et al. | |
| 2010/0016694 A1 | 1/2010 | Martin et al. | |
| 2010/0028026 A1 | 2/2010 | Inami et al. | |
| 2010/0106246 A1 | 4/2010 | Rousseau et al. | |
| 2010/0108066 A1 | 5/2010 | Martin et al. | |
| 2010/0108077 A1 * | 5/2010 | Lindh | A61F 5/566 128/848 |
| 2010/0132719 A1 * | 6/2010 | Jacobs | A61F 5/566 128/848 |
| 2010/0144701 A1 | 6/2010 | Cooper et al. | |
| 2010/0234946 A1 | 9/2010 | Rousseau | |
| 2010/0300458 A1 | 12/2010 | Stubbs et al. | |
| 2011/0056498 A1 | 3/2011 | Lang et al. | |
| 2011/0094520 A1 | 4/2011 | Mikhailenok et al. | |
| 2011/0100376 A1 | 5/2011 | Rousseau | |
| 2011/0100378 A1 | 5/2011 | Rousseau | |
| 2011/0130249 A1 | 6/2011 | Mikhailenok et al. | |
| 2011/0166673 A1 | 7/2011 | Patel et al. | |
| 2011/0183928 A1 | 7/2011 | Thede et al. | |
| 2011/0226264 A1 | 9/2011 | Friedman | |
| 2011/0245850 A1 | 10/2011 | van der Burg et al. | |
| 2011/0308530 A1 | 12/2011 | Gillis et al. | |
| 2013/0056009 A1 | 3/2013 | Mohan et al. | |
| 2013/0085546 A1 | 4/2013 | Bolea et al. | |

(56) References Cited

U.S. PATENT DOCUMENTS

| | | |
|---|---|---|
| 2013/0180528 A1 | 7/2013 | Zhou et al. |
| 2013/0213409 A1 | 8/2013 | Podmore et al. |
| 2014/0102460 A1 | 4/2014 | Catalano |

FOREIGN PATENT DOCUMENTS

| | | |
|---|---|---|
| WO | 2007149469 A2 | 12/2007 |
| WO | 2009140197 | 11/2009 |
| WO | 2010045546 | 4/2010 |
| WO | 2010051195 | 5/2010 |
| WO | 2011068952 | 6/2011 |
| WO | 2011068952 A1 | 6/2011 |
| WO | 2011123714 | 10/2011 |
| WO | 2013010169 | 1/2013 |
| WO | 2013010169 A1 | 1/2013 |

OTHER PUBLICATIONS

International Searching Authority, International Search Report and the Written Opinion, for International Application No. PCT/US2012/046923, dated Nov. 2, 2012, p. 1-18.

File history of U.S. Appl. No. 08/883,220, now U.S. Pat. No. 5,988,171, as of Nov. 21, 2013, filed Jun. 26, 1997. First Named Inventor, Ze'ev Sohn. Title, Methods and Devices for the Treatment of Airway Obstruction, Sleep Apnea and Snoring.

File history of U.S. Appl. No. 10/877,003, now U.S. Pat. No. 7,213,599, as of Nov. 21, 2013, filed Jun. 24, 2004. First Named Inventor, Timothy R. Conrad. Title, Airway Implant.

File history of U.S. Appl. No. 11/757,501, now U.S. Pat. No. 7,703,460, as of Nov. 21, 2013, filed Jun. 4, 2007. First Named Inventor, Timothy R. Conrad. Title, Tongue Implant.

File history of U.S. Appl. No. 12/214,084, as of Nov. 21, 2013, filed Jun. 17, 2008. First Named Inventor, Octavian Iancea. Title, Implantable devices, systems, and methods for maintaining desired orientations in targeted tissue regions.

International Searching Authority, International Preliminary Report on Patentability, for International Application No. PCT/US2012/046923, dated Jan. 23, 2014, p. 1-7.

Woodson et al. Multicenter study of a novel adjustable tongue-advacement device for obstructive sleep apnea [article]. Otolaryngology—head and neck surgery, vol. 143, No. 4, pp. 585-590. IP: 128.210.125.135. Jun. 10, 2010. SAGE.

Woodson et al. Response to: Multicenter study of a novel adjustable tongue-advancement device for obstructive sleep apnea [article]. Otolaryngology—head and neck surgery, vol. 144, No. 6, pp. 1009-1012. 2011. SAGE.

Siesta Medical. Siesta Medical receives 510(k) clearance for Encore system to treat obstructive sleep apnea [press release]. Sep. 12, 2011. pp. 1-2.

Aspire Medical, Inc. Aspire Medical announces first implant in US and start of clinical trial to treat sleep apnea [article]. Medical News Today. May 23, 2007. pp. 1-4. URL: <http://www.medicalnewstoday.com/releases/71787.php>.

Hamans et al. A novel tongue implant for tongue advancement for obstructive sleep apnea: feasibility, safety and histology in a canine model [article]. J Musculoskelet Neuronal Interact. vol. 10, No. 1, pp. 100-111. Dec. 29, 2009. Hylonome.

Knobbe, Martens, Olson & Bear, LLP. Amendment and response to non-Final Office Action dated Jan. 16, 2013, for U.S. Appl. No. 13/077,813, filed Mar. 31, 2011. First Named Inventor, van der Burg. Title, Suture Passer Systems and Methods for Tongue or Other Tissue Suspension and Compression.

PR Newswire. Asprie Medical appoints Roseanne Varner as president and CEO [press release]. pp. 1-2. May 1, 2011. URL: <http://www.prnewswire.com/news-releases/aspire-medical-appoints-roseanne-varner-as-president-and-ceo-57760852.html>.

Park. Aspire Medical Advance System for obstructive sleep apnea [blog]. Dr. Park: Breathe better, sleep better, live better. pp. 1-4. Oct. 6, 2010. URL: <http://doctorstevenpark.com/aspire-medical-advance-system-for-obstructive-sleep-apnea>.

Revent Medical. The Revent Solution: Tongue Implanter Kit [webpage]. 2014. pp. 1-2. Retrieved Aug. 12, 2014. URL: <http://www.reventmedical.com/solution/>.

Revent Medical. The Revent Solution: Implants [webpage]. 2014. pp. 1-2. Retrieved Aug. 12, 2014. URL: <www.reventmedical.com/solution/>.

European Patent Office, Examination Report for European Application No. 14752978.8; Mar. 31, 2017.

\* cited by examiner

TISSUE ADJUSTMENT IMPLANT

RELATED APPLICATION

This application claims the benefit of U.S. Provisional Application No. 61/861,089, filed on Aug. 1, 2013. The disclosure of this related application is hereby incorporated into this disclosure in its entirety.

FIELD

The disclosure relates generally to the field of implantable medical devices. Particular embodiments relate to tissue adjustment implants.

BACKGROUND

It is sometimes necessary or desirable to secure a tissue or portion of a tissue within the body of an animal, such as a human, in a manner that temporarily or permanently adjusts a position or orientation of the tissue or portion of a tissue. For example, in the treatment of Obstructive Sleep Apnea (OSA), it may be desirable to adjust the position of one or more tissues or portions of tissue, such as the soft palate.

OSA is a clinical disorder in which a partial or complete collapse of soft tissue occurs in the airway during sleep. This leads to a blockage of the airway and impaired breathing during sleep. Mild OSA can lead to fatigue, reduced alertness following sleep, and a general reduction in productivity for the affected individual. Severe OSA can lead to sleep deprivation, hypoxemia, and depression.

The art provides various options for the treatment of OSA. Continuous Positive Airway Pressure (CPAP) machines, which supply positive air pressure through a facemask and into the airway during sleep, are used most frequently. The positive air pressure maintains an open airway to prevent apnea and snoring. While these machines are generally considered effective, they are bulky, noisy, and cumbersome to use. Furthermore, use of these machines can be socially awkward for some individuals.

Oral appliances that force the jaw forward to maintain an open airway can also be used. These devices are generally considered to be not as effective as CPAP machines, and can be uncomfortable to use. Furthermore, these devices are frequently ejected from the mouth during sleep, reducing their effectiveness over the entire course of a sleeping period.

Invasive surgical procedures can also be used to treat OSA. Various techniques have been described, including uvulopalatopharyngoplasty (UPPP), maxillomandibular advancement (MMA), and even tracheostomy. Surgical procedures are generally considered to have limited and potentially short-lived effectiveness. Furthermore, many of the procedures require hospitalization and the use of general anesthesia. As a result, these procedures are generally reserved for severe cases of OSA.

The AIRvance™ System from Medtronic, formerly known as the Repose System, provides a surgical-based tongue suspension procedure that can be performed with or without an adjunct hyoid suspension procedure. These suspension procedures require a surgical incision and dissection of the neck below the mandible. Following implantation of one or more necessary bone screws, sutures are lashed around the tongue and/or hyoid bone and secured with surgical knots. While these procedures offer less complicated solutions than the surgical procedures above, they still require surgical intervention and suffer from the drawbacks associated with surgical procedures. Furthermore, over time, the sutures used to suspend the tongue and/or hyoid bone may weaken or even snap, which may limit the effectiveness of the treatment over time. Lastly, the use of sutures in these procedures necessitates the use of specialized knotting and securement techniques to complete the procedure, which adds an additional opportunity for error and failure in the device and the procedure.

Considering the disadvantages of the various available treatment options described above, a need exists for improved devices for adjustment of tissue within the body. Furthermore, a need exists for additional options, including implantable medical devices, for the treatment of OSA.

DESCRIPTION OF EMBODIMENTS

The following detailed description and the appended drawings describe and illustrate various example embodiments. The description and illustration of these examples are provided to enable one skilled in the art to make and use a tissue adjustment implant. They are not intended to limit the scope of the claims in any manner.

Figure 1:
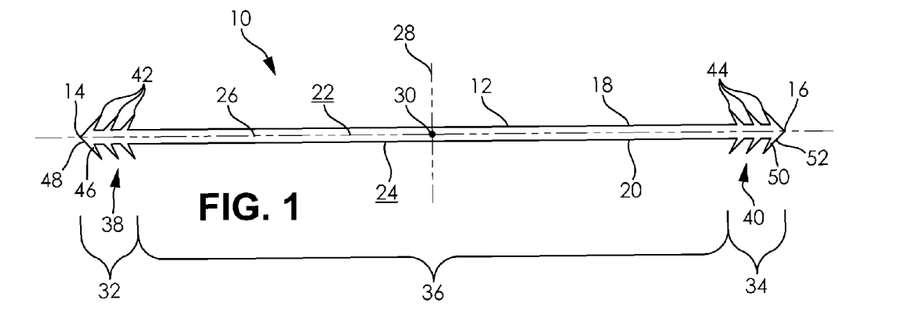
FIG. 1 is a perspective view of an embodiment of a tissue adjustment implant.

FIG. 1 illustrates an example of a tissue adjustment implant 10. The tissue adjustment implant 10 has a main body 12 comprising a substantially flat member extending from a first end 14 to an opposing second end 16 and having first 18 and second 20 opposing sides. The main body 12 has a first 22 or upper surface and an opposing second 24 or lower surface.

The main body 12 has a lengthwise axis 26 and a transverse axis 28 that orthogonally intersects the lengthwise axis 26 at a longitudinal midpoint 30 disposed on the lengthwise axis 26. A first anchor portion 32 extends along the lengthwise axis 26 of the main body 12 from a point on the lengthwise axis 26 between the longitudinal midpoint 30 and the first end 14 to the first end 14. Similarly, a second anchor portion 34 extends along the lengthwise axis 26 of the main body 12 from a point on the lengthwise axis 26 between the longitudinal midpoint 30 and the second end 16 to the second end 16. A middle portion 36 extends along the lengthwise axis 26 of the main body 12 across the longitudinal midpoint 30 from an end of the first anchor portion 32 to an end of the second anchor portion 34.

The first anchor portion 32 defines a first series of projections 38. Similarly, the second anchor portion 34 defines a second series of projections 40. Each of the first 38 and second 40 series of projections includes a series of projections that extend outwardly from the respective side 18, 20 of the main body 12, away from the longitudinal axis 26. The middle portion 36 is free of outwardly extending projections.

As used herein, the term "projection" refers to an outwardly-directed member or portion of a member that extends away from a surface of another member or another portion of a member. An individual projection can have any suitable shape, including regular and irregular shapes, symmetrical and asymmetrical shapes, and any other suitable shape. The term "series of projections" refers to two or more individual projections. A series of projections includes multiple projections having the same shape, size and or/configurations, a series of projections having different sizes, shapes and configurations, a series of projections spaced at regular intervals, such as a toothed surface, a series of projections spaced at different intervals, and a series of projections spaced at irregular intervals. The illustrated embodiment includes a series of projections extending away from each side 18, 20 of the main body in each series of projections 38, 40. It is understood, though, that any suitable number of projections can extend away from each side 18, 20 of the main body 12 in a series of projections, including one projection, two projections, three projections, or more. Indeed, the number of projections that extend away from a side 18, 20 in a series of projections need only be at least one projection. Furthermore, it is noted that a series of projections can include one or more projections that extend away from only one of the sides 18, 20 of the main body 12 or away from both of the sides 18, 20 of the main body 12.

In the illustrated embodiment, each projection 42 of the first series of projections 38 is substantially triangular in shape and extends away from the longitudinal axis 26 and away from the first end 14 of the main body 12 toward the transverse axis 28. Similarly, each projection 44 of the second series of projections 40 is substantially triangular in shape and extends away from the longitudinal axis 26 and away from the first end 14 of the main body 12 toward the transverse axis 28.

In the illustrated embodiment, a projection 46 of the first series of projections 38 that is farthest from the longitudinal midpoint 30 has a side 48 that is continuous with the first end 14 of the main body 12. Similarly, a projection 50 of the second series of projections 40 that is farthest from the longitudinal midpoint 30 has a side 52 that is continuous with the second end 16 of the main body 12.

Inclusion of the opposing series of projections 38, 40 is considered advantageous at least because each series 38, 40 provides an anchor at an end of the tissue adjustment implant 10 that is opposite an end of the implant that is first inserted into the tissue. Once the tissue adjustment implant 10 is then passed through the tissue, the series of projections at the opposite end are able to engage the tissue and, upon the application of additional force on the tissue engaging implant, such as tension, the position of the tissue can be adjusted, such as by lifting or otherwise moving the tissue, as described more fully below. As an example, described in greater detail below, the tissue adjustment implant can be used to engage and adjust the position of the soft palate of a patient, such as in the treatment of Obstructive Sleep Apnea.

In the illustrated embodiment, the first 22 and second 24 surfaces of the main body 12 are substantially flat. It is noted, though, that it may be advantages to include one or more bumps, projections or other surface modifications on one or both of the surfaces 22, 24. Inclusion of such modifications may improve the handling of the tissue adjustment implant 10 during use.

Figure 2:
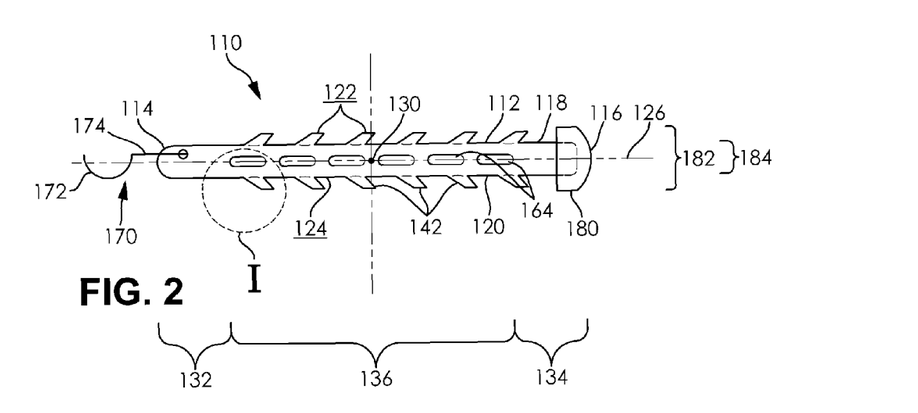
FIG. 2 is a perspective view of another embodiment of a tissue adjustment implant.
Figure 2A:
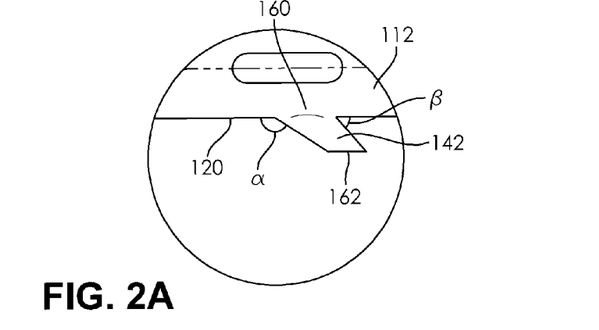
FIG. 2A is a magnified view of area I indicated in FIG. 2.

FIGS. 2 and 2A illustrate another tissue adjustment implant 110. In this embodiment, the tissue adjustment implant 110 comprises a main body 112 comprising a substantially flat member extending from a first end 114 to an opposing second end 116 and having first 118 and second 120 opposing sides. The main body 112 has a first 122 or upper surface and an opposing second 124 or lower surface. The main body 112 has a lengthwise axis 126 and a transverse axis 128 that orthogonally intersects the lengthwise axis 126 at a longitudinal midpoint 130 disposed on the lengthwise axis 126. An anchor portion 136 extends along the lengthwise axis 126 of the main body 112 across the longitudinal midpoint 130. A first end portion 132 extends from an end of the first anchor portion 132 to the first end 114 of the main body 112. A second end portion 134 extends from the opposite end of the anchor portion 132 to the second end 116 of the main body 112.

In this embodiment, the anchor portion 136 defines a first series of projections 138 and a second series of projections 140. Each of the first 138 and second 140 series of projections includes a series of projections that extend outwardly from the respective side 118, 120 of the main body 112, away from the longitudinal axis 126. The first 132 and second 134 end portions are free of outwardly extending projections.

As best illustrated in FIG. 2A, each projection 142 of the first 138 and second 140 series of projections is a wing-shaped member that extends radially outward from a side 120 of the main body 112. The wing-shaped member has a relatively wide base 160 that lies along a hypothetical extension of the side 120 and a relatively narrow end 162 that lies on hypothetical line that is parallel to the side 120. As best illustrated in FIG. 2, each projection 142 of the first 138 and second 140 series or projections extends away from the respective side 118, 120 and away from the first end 114 of the main body. In the illustrated embodiment, as best illustrated in FIG. 2A, each projection 142 of the first 138 and second 140 series of projections extends away from the respective side 118, 120 of the main body at an angle such that an obtuse angle α is formed on the side of the projection 142 that is closest the first end 114 of the main body 112 and such that an acute angle β is formed on the side of the projection 142 that is closest the second end 116 of the main body 112. While any suitable configuration can be used for the projections 142, this configuration facilitates placement and anchoring.

In this embodiment, the main body 112 defines a series of openings 164 positioned along the lengthwise axis 126. Each opening of the series of openings 164 extends through the thickness of the main body 112 from the first surface 122 to the second surface 124. As such, each opening defines a passageway that extends through the main body 112. In this embodiment, as best illustrated in FIG. 2, the series of openings 164 extends along the entire anchor portion 136 of the main body 112.

It is noted that any opening in the series of openings 164 can have one or more dimensions that differ from the same dimension or dimensions of another opening in the series of openings 164 while also have one or more dimension that is the same or substantially similar to the same dimension or dimensions of the other openings of the series of openings 164. For example, each opening of the series of openings 164 may have a rectangular shape, with one or more opening having a length and width that differ from the length and width of one or more other rectangular-shaped openings. Also, while the illustrated embodiment includes a series of openings 164, it is noted that any suitable number of openings can be included in a tissue adjustment implant according to a particular embodiment, including zero, one, two, three, or any other suitable number of openings. Inclusion of one or more openings facilitates anchoring of a tissue adjustment implant following implantation.

In this embodiment, a lead 170 is attached to the first end 114 of the main body. The lead 170 provides a leading structure that can be used to form an opening in and/or introduce the tissue adjustment implant into tissue. As such, the lead 170 advantageously includes a portion that can cut into tissue. For example, in the illustrated embodiment, the lead 170 comprises a needle 172 secured to a suture 174 that is attached to the main body 112 near the first end 114. It is noted, though, that any suitable lead structure can be used, including a cutting edge or point that is disposed in the first end of a main body of tissue adjustment implant.

In this embodiment, a plug 180 is disposed on the second end 116 of the main body 112. The plug 180 has a width 182 that is greater than a width 184 of the main body 112 measured from one side 118 to the other 120. In the illustrated embodiment, the plug 180 is a separate member that has been attached to the main body, such as by an adhesive or through mechanical attachment. It is noted, though, that in other embodiments the plug can be integrally formed with the main body.

Inclusion of a plug on an end of the main body facilitates implantation of a tissue adjustment implant because it provides a mechanical stop that impedes further passage of the tissue adjustment implant into the tissue once the plug has reached the point of entry into the tissue, such as an opening through which the remainder of the tissue adjustment implant has been passed. Also, by providing a mechanical stop that impedes further passage of the tissue adjustment implant, the inclusion of a plug facilitates the adjustment function of the tissue adjustment implant. For example, once the plug has reached the point of entry into the tissue, a continued pulling on the tissue adjustment implant, such as a continued pulling on lead attached to the first end of the main body or on the first end of the main body itself, will produce a pulling force on the tissue surrounding the plug at the point of entry. This can be used to lift, move or otherwise adjust the position of the tissue within the body through the application of a simple pulling force on the tissue adjustment implant.

Figure 3A:
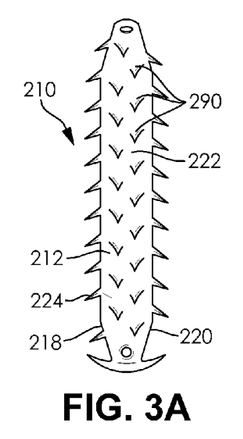
FIG. 3A is a perspective view of another embodiment of a tissue adjustment implant.

Each of FIGS. 3A, 3B, 3C, 3D, and 3E illustrates a tissue adjustment implant that includes an alternative structure for a series of projections. FIG. 3A illustrates a tissue adjustment implant 210 that includes a flat main body 212 into which a series of projections 290 has been formed by cutting through the thickness of the main body 212. This forms projections that can extend outward from one 222 or the other 224 surfaces of the main body 212. Any suitable technique can be used to form the projections in this manner, including die cutting and laser cutting techniques. The specific technique selected for a particular embodiment with depend on various considerations, including the material of the main body and the size and configuration of the projections. Laser cutting is a suitable technique for forming projections in a main body that comprises a flat sheet, such as a flat sheet of small intestine submucosa. Additional projections extend radially outward from the sides 218, 220 of the main body 212.

Figure 3B:
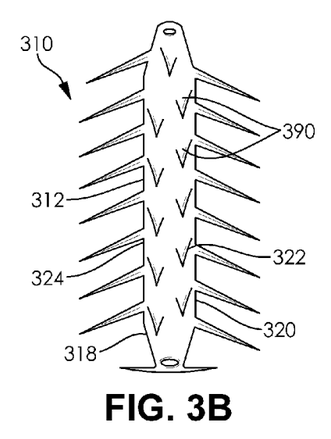
FIG. 3B is a perspective view of another embodiment of a tissue adjustment implant.

Any suitable angle, length, shape and configuration can be used for the projections. FIG. 3B illustrates a tissue adjustment implant 310 that has projections that are similar in shape to those of the tissue adjustment implant 210 illustrated in FIG. 3A, but that are relatively larger. In this embodiment, a series of projections 390 has been formed by cutting through the thickness of the main body 312. This forms projections that can extend outward from one 322 or the other 324 surfaces of the main body 312. Additional projections extend radially outward from the sides 318, 320 of the main body 312.

Figure 3C:
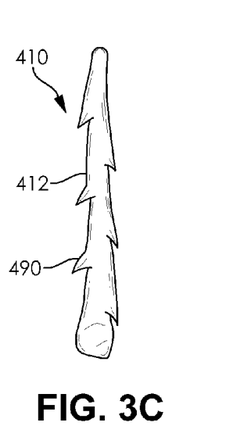
FIG. 3C is a perspective view of another embodiment of a tissue adjustment implant.

FIG. 3C illustrates a tissue adjustment implant 410 that includes a substantially round, elongate main body 412. A series of projections 490 has been formed by cutting into the main body 412 at an angle to form a wedge-shaped projection. Each projection of the series of projections has been pulled slightly away from the main body 412.

Figure 3D:
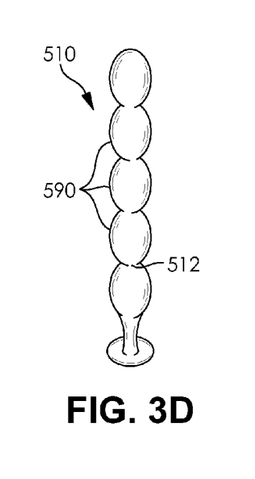
FIG. 3D is a perspective view of another embodiment of a tissue adjustment implant.

FIG. 3D illustrates a tissue adjustment implant 510 that includes a series of projections 590 that is integrally formed with the main body 512. Each projection of the series of projections comprises a substantially circular-shaped body. In this embodiment, along with other embodiments in which the projections are integrally formed with the main body, the projections can be formed during the process of forming the main body, such as in a molding technique.

Figure 3E:
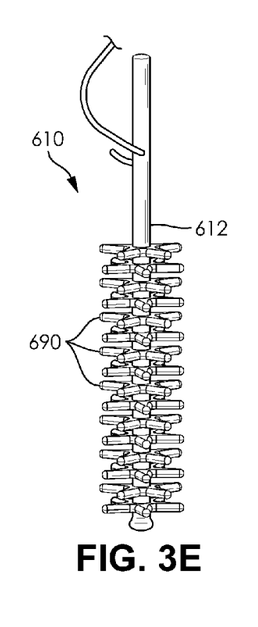
FIG. 3E is a perspective view of another embodiment of a tissue adjustment implant.
Figure 3F:
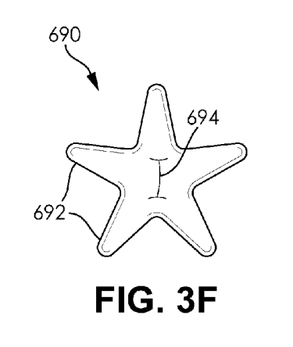
FIG. 3F is a perspective view of a projection member isolated from the implant illustrated in FIG. 3E.

FIG. 3E illustrates a tissue adjustment implant 610 in which a series of separate projection-defining members 690 have been passed over a main body 612. FIG. 3F illustrates a single projection-defining member 690 isolated from the tissue adjustment implant. As best illustrated in that Figure, each projection-defining member 690 defines outwardly-extending projections 692 and an opening 694. The tissue adjustment implant 610 is formed by passing the main body 612 through the opening 694 of each of a series of projection-defining members 690. Once disposed on the main body 612, the projection-defining members can be rotated about its lengthwise axis to place the projections in an offsetting relationship with respect to each other. While a series of projection-defining members 690 is illustrated, it is noted that any suitable number can be used, including one, two, three or any suitable number. Also, while the illustrated projection-defining members 690 are star-shaped, any suitable shape, size and configuration can be used, including any configuration that provides the desired outwardly-extending projections.

It is noted that, while not illustrated in the Figures, any of the tissue adjustment implants illustrated in FIGS. 3A, 3B, 3C, 3D and 3E can include any suitable lead attached to the main body, as described above, as well as any suitable plug, as described above and below.

If included, the plug can have any suitable size, shape and configuration. Indeed, the plug in a tissue adjustment implant according to a particular embodiment need only have sufficient structure to provide the desired mechanical stop, as described above. Each of FIGS. 4A, 4B, 4C, 4D, and 4E illustrates a tissue adjustment implant that includes an example structure for a plug.

Figures 4A, 4B:
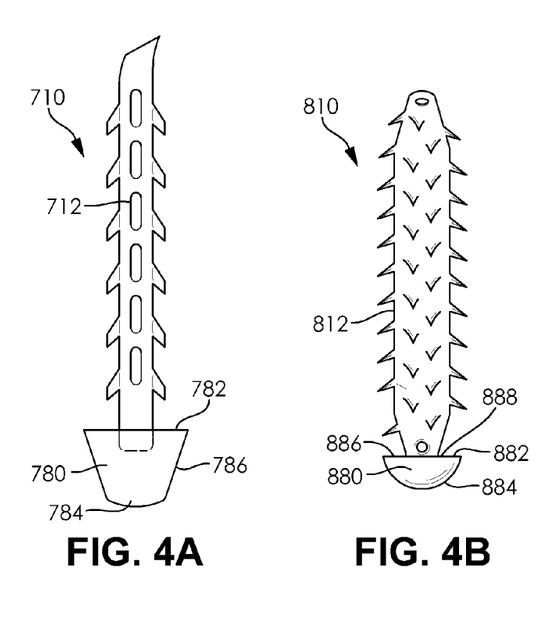
FIG. 4A is a perspective view of another embodiment of a tissue adjustment implant.
FIG. 4B is a perspective view of another embodiment of a tissue adjustment implant.

FIG. 4A illustrates a tissue adjustment implant 710 that includes a plug 780 that is integrally formed with the main body 712 of the tissue adjustment implant 710. In this embodiment, the plug 780 has a stopper configuration, with a base 782, an end 784, and a frustoconical wall 786 that extends between the base 782 and end 784. The base 782 and end 784 are flat and parallel with each other.

FIG. 4B illustrates a tissue adjustment implant 810 that includes a plug 880 that comprises a separate element that has been attached to the main body 812 of the tissue adjustment implant 810. In this embodiment, the plug 880 has a rounded button configuration, with a base 882 and a rounded end 884 that meets the base 882 at outer edge 886 of the base 882. The plug 880 can be attached to the main body 812 by forming an opening 888 in a section of material, such as excess material from the forming of the main body 812, and placing an end 816 of the main body into the opening 888. An adhesive or other suitable agent for securing the plug 880 to the main body 812, can be added to the connection, such as in the opening 882, around an interface between the plug 880 and main body 812, or both.

Figure 4C:
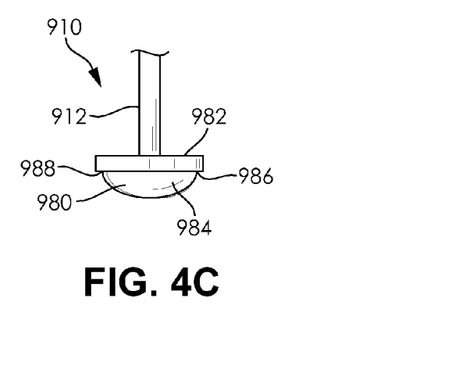
FIG. 4C is a perspective view of another embodiment of a tissue adjustment implant.

FIG. 4C illustrates a tissue adjustment implant 910 that includes a plug 980 that is integrally formed with the main body 912 of the tissue adjustment implant. In this embodiment, the plug 980 has a flattened button configuration, with a base 982 and a rounded end 984 that meets the base 982 at a point that is radially inward from the outer edge 986 of the base 982. This forms a circumferential shoulder 988 that extends around the plug 980 slightly inward from the outer edge 986 of the base 982. The plug 980 can be formed with the main body 912 by including a partial spherical or other rounded chamber, adjacent a chamber of appropriate size and configuration for forming the base 982, in the forming of the main body 912.

Figure 4D:
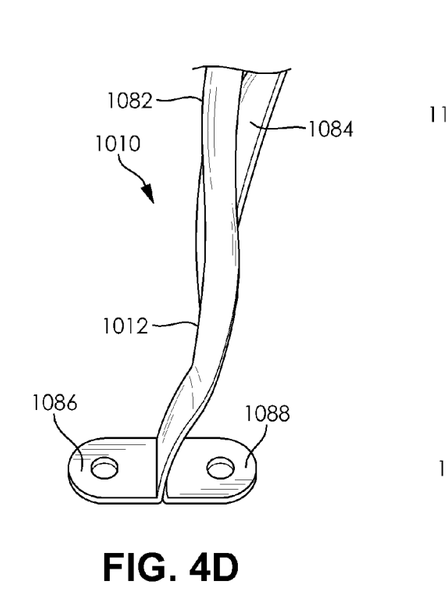
FIG. 4D is a perspective view of another embodiment of a tissue adjustment implant.

FIG. 4D illustrates a tissue adjustment implant 1010 that includes a main body 1012 formed of multiple sheets 1082, 1084 of material that have been attached to each other. In this embodiment, the plug 1080 comprises an end portion 1086 of the first 1082 sheet and an end portion 1088 of the second 1084 sheet that have been separated from each other and coated with a stiffening or other suitable agent, such as PLGA, to maintain their separated position. In the illustrated embodiment, the end portions 1086, 1088 have been positioned at orthogonal angles to the longitudinal axis of the main body 1012, but it is noted that any suitable angle can be used, including a substantially orthogonal angle, an obtuse angle, or an acute angle. Also, it is noted that, while described as having been separated from each other after the sheets 1082, 1084 have been attached to each other, the end portions 1086, 1088 can also be positioned as described prior to other portions of the sheets 1082, 1084 being attached to each other. Lastly, while described as first 1082 and second 1084 sheets, one or both of the sheets can comprise a group of two or more sheets, such as a series of sheets.

Figure 4E:
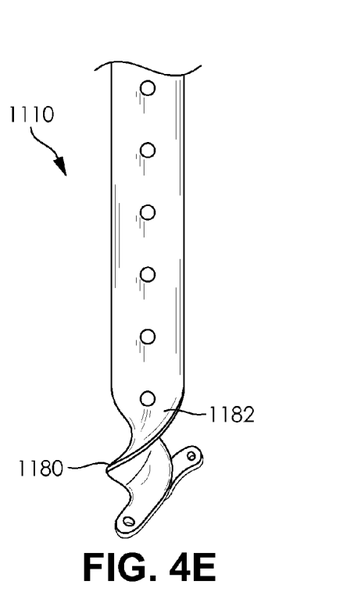
FIG. 4E is a perspective view of another embodiment of a tissue adjustment implant.

FIG. 4E illustrates a tissue adjustment implant 1110 that includes a plug 1180 that comprises a simple knot tied an end portion 1182 of the main body 1112. Thus, even if a tissue adjustment implant according to a particular embodiment doesn't initially include a plug, a user can form a plug at or near the time of use, if desired.

Figure 6:
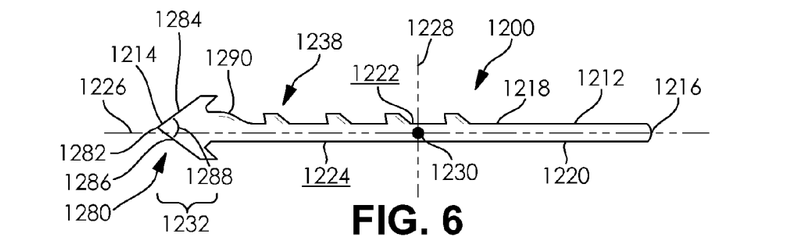
FIG. 6 is a top view of another embodiment of a tissue adjustment implant.
Figure 6A:
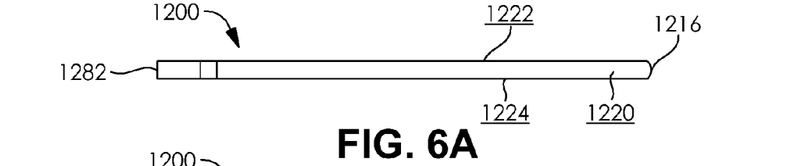
FIG. 6A is an elevation view of the tissue adjustment implant illustrated in FIG. 6.
Figure 6B:
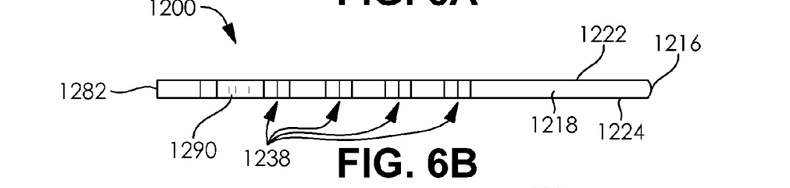
FIG. 6B is another elevation view of the tissue adjustment implant illustrated in FIG. 6.

FIGS. 6, 6A and 6B illustrate another example of a tissue adjustment implant 1200. The tissue adjustment implant 1200 has a main body 1212 comprising a substantially flat member extending from a first end 1214 to an opposing second end 1216 and having first 1218 and second 1220 opposing sides. The main body 1212 has a first 1222 or upper surface and an opposing second 1224 or lower surface. The main body 1212 has a lengthwise axis 1226 and a transverse axis 1228 that orthogonally intersects the lengthwise axis 1226 at a longitudinal midpoint 1230 disposed on the lengthwise axis 1226. A first anchor portion 1232 is disposed on the first end 1214 of the main body 1212 and defines an arrowhead 1280 having a terminal point 1282. First 1284 and second 1286 sides of the arrowhead 1280 are oriented at angle 1288 with respect to each other. In contrast to some of the examples described above, the second end 1216 in the example embodiment does not include a plug or other terminal structure, although inclusion of a plug or other suitable structure may be desirable in certain embodiments.

A series of projections 1238 extends from one side 1218 of the main body 1210. The other side 1220 is substantially flat and contains no projections. Thus, in this embodiment, projections extend from only one side of the main body 1210. Also, each of the projections in the series of projections 1238 extends away from the main body 1210, away from the second end 1216. Also, the first 1284 and second 1286 sides of the arrowhead 1280 extend away from the main body 1210 and away from the first end 1214.

The main body 1210 includes a throat portion 1290 that transitions from the width of the base of the arrowhead 1280 to the width of the main body 1210, taken from the first side 1218 to the second side 1220. The inventors have determined that inclusion of the throat portion 1290 provides desirable loading and implantation properties.

The inventors have determined that the inclusion of the arrowhead 1280 and the series of projections 1238 on one side 1218 on the tissue adjustment implant 1200 provides desirable anchoring characteristics while maintaining a low profile structure that facilitates implantation and retention.

The tissue adjustment implant 1200 can be formed as an integral unit that defines the main body, series of projections, first anchor portion, and throat portion. In these embodiments, an integral unit formed as a multi-laminate construct, as described below, is considered advantageous. Alternatively, the tissue adjustment implant 1200 can be formed as separate portions that are attached or otherwise secured to each other. For example, a main body can be formed with the projections, and an anchor portion, such as an anchor portion that defines an arrowhead, can be attached or otherwise secured to an end of the main body to form a tissue adjustment implant.

Figure 7:
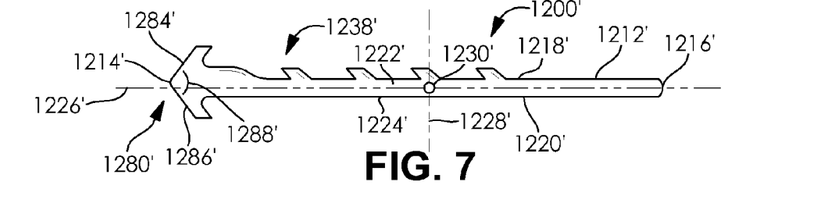
FIG. 7 is a top view of another embodiment of a tissue adjustment implant.
Figure 8:
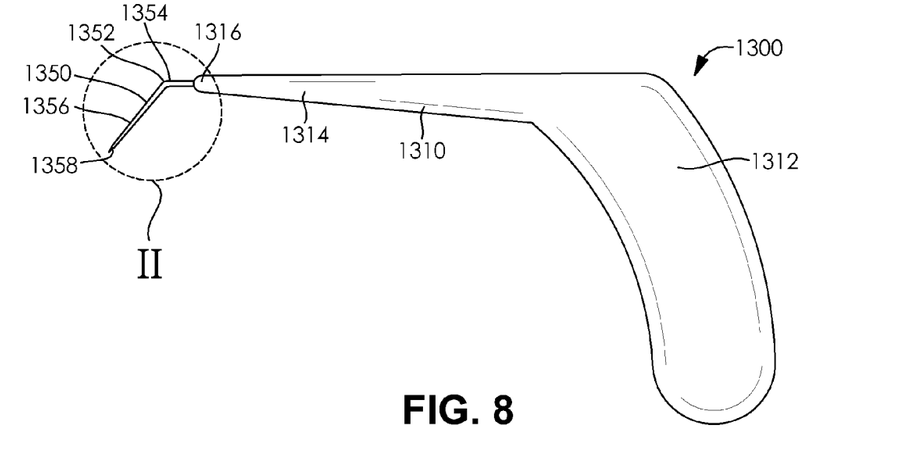
FIG. 8 is an elevation view of a delivery device for implanting a tissue adjustment implant.

FIG. 7 illustrates an alternate tissue adjustment implant 1200'. The tissue adjustment implant 1210' according to this embodiment is the same as the tissue adjustment implant 1200 described above and illustrated in FIGS. 6, 6A, and 6B, except as detailed below. Thus, the tissue adjustment implant 1200' has a main body 1212' comprising a substantially flat member extending from a first end 1214' to an opposing second end 1216' and having first 1218' and second 1220' opposing sides. The main body 1212' has a first 1222' or upper surface and an opposing second 1224' or lower surface. The main body 1212' has a lengthwise axis 1226' and a transverse axis 1228' that orthogonally intersects the lengthwise axis 1226' at a longitudinal midpoint 1230' disposed on the lengthwise axis 1226'. A first anchor portion 1232' is disposed on the first end 1214' of the main body 1212' and defines an arrowhead 1280' having a terminal point 1282'. A series of projections 1238' extends from one side 1218' of the main body 1210'. The other side 1220' is substantially flat and contains no projections. Thus, in this embodiment, projections extend from only one side of the main body 1210'. Also, each of the projections in the series of projections 1238' extends away from the main body 1210', away from the second end 1216'. Also, the first 1284' and second 1286' sides of the arrowhead 1280' extend away from the main body 1210' and away from the first end 1214'. The main body 1210' includes a throat portion 1290' that transitions from the width of the base of the arrowhead 1280' to the width of the main body 1210', taken from the first side 1218' to the second side 1220'.

In this embodiment, the terminal point 1282' of the arrowhead 1280' is a rounded point. Also in this embodiment, the first 1284' and second 1286' sides of the arrowhead 1280' are oriented at angle 1288' with respect to each other. The angle 1288' of this embodiment is relatively broad, or obtuse, as compared to the angle 1288 in the embodiment illustrated in FIGS. 6, 6A, and 6B.

In a tissue adjustment implant according to a particular embodiment that includes an anchor portion that defines an arrowhead, the sides of the arrowhead can be oriented with respect to each other at any suitable angle. A skilled artisan will be able to determine a suitable angle for a tissue adjustment implant according to a particular embodiment based on various considerations, including the nature of the tissue within which the tissue adjustment implant is intended to be used, the material forming the tissue adjustment implant, and other considerations. The inventors have determined that an acute angle, such as angle 1288 illustrated in FIG. 6, facilitates initial passage of the tissue adjustment implant 1280 into tissue during implantation, but provides a relatively low degree of anchoring or resistance to reverse movement following implantation. In contrast, the inventors have determined that an obtuse angle, such as angle 1288' illustrated in FIG. 7, requires additional force to accomplish the initial passage of the tissue adjustment implant 1280' into tissue during implantation, but provides a relatively high degree of anchoring or resistance to reverse movement following implantation. Based on these considerations, the a skilled artisan will be able to select a suitable angle for inclusion in a tissue adjustment implant according to a particular embodiment.

Examples of suitable angles include an acute angle and an obtuse angle. Acute angles between about 15 degrees and about 90 degrees are also considered suitable. Acute angles between about 35 degrees and about 90 degrees are also considered suitable. Acute angles between about 45 degrees and about 90 degrees are also considered suitable. Acute angles between about 55 degrees and about 90 degrees are also considered suitable. Acute angles between about 65 degrees and about 90 degrees are also considered suitable. Acute angles between about 75 degrees and about 90 degrees are also considered suitable. Acute angles between about 85 degrees and about 90 degrees are also considered suitable. The inventors have determined that an acute angle of about 45 degrees provides a desirable balance between the force required to achieve initial passage of a tissue adjustment implant into tissue during implantation and the degree of anchoring or resistance to reverse movement following implantation. Furthermore, the inventors have determined that an acute angle of 45 degrees provides a desirable balance between the force required to achieve initial passage of a tissue adjustment implant into tissue during implantation and the degree of anchoring or resistance to reverse movement following implantation.

Obtuse angles between about 90 degrees and about 105 degrees are also considered suitable. Obtuse angles between about 90 degrees and about 115 degrees are also considered suitable. Obtuse angles between about 90 degrees and about 125 degrees are also considered suitable. Obtuse angles between about 90 degrees and about 135 degrees are also considered suitable. Obtuse angles between about 90 degrees and about 145 degrees are also considered suitable. Obtuse angles between about 90 degrees and about 155 degrees are also considered suitable. Obtuse angles between about 90 degrees and about 165 degrees are also considered suitable. The inventors have determined that an obtuse angle of about 135 degrees provides a desirable balance between the force required to achieve initial passage of a tissue adjustment implant into tissue during implantation and the degree of anchoring or resistance to reverse movement following implantation. Furthermore, the inventors have determined that an obtuse angle of 135 degrees provides a desirable balance between the force required to achieve initial passage of a tissue adjustment implant into tissue during implantation and the degree of anchoring or resistance to reverse movement following implantation.

A right angle is also considered suitable. The inventors have determined that an angle of about 90 degrees is suitable. Furthermore, the inventors have determined that an angle of 90 degrees is suitable.

FIGS. 8, 9, 10, and 11 illustrate an example delivery device 1300 suitable for implanting a tissue adjustment implant in a tissue of a patient, such as the soft palate of a human being. The delivery device 1300 comprises a main body 1310 defining a handle 1312 that can be gripped by a user. The main body also defines a barrel 1314 that extends away from the handle 1312. A cannula 1350 is disposed in the distal end 1316 of the main body 1310 such that the cannula 1350 extends away from the main body 1310. In the illustrated embodiment, the cannula 1350 defines a bend 1352 such that a first portion 1354 of the cannula 1350 extends substantially along an axis of the barrel 1314 and a second portion 1356 of the cannula 1350 extends away from the axis of the barrel 1314. The second portion 1356 of the cannula 1350 defines a notch 1358.

Figure 9:
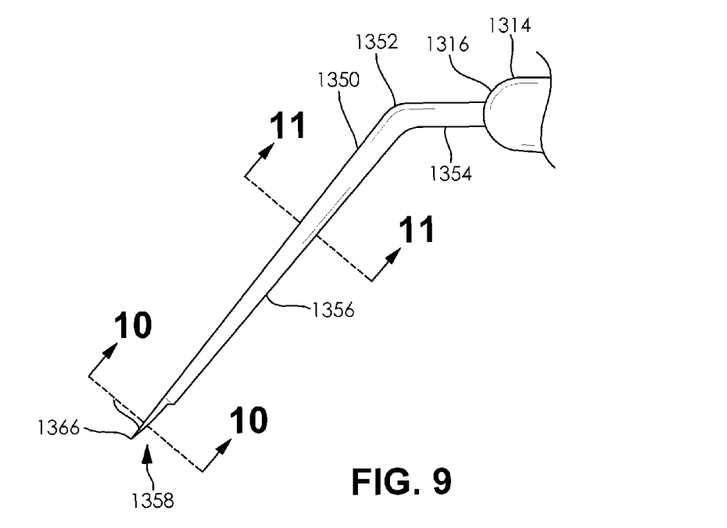
FIG. 9 is a magnified view of area II illustrated in FIG. 8.
Figure 10:
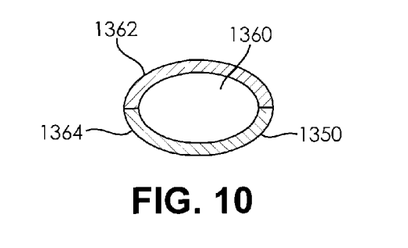
FIG. 10 is a sectional view of the cannula of the delivery device illustrated in FIG. 9, taken along line 10-10.
Figure 11:
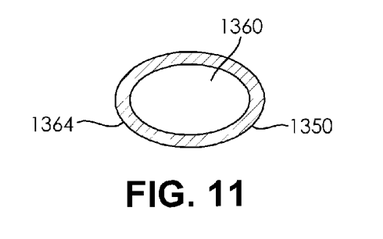
FIG. 11 is a sectional view of the cannula of the delivery device illustrated in FIG. 9, taken along line 11-11.

As best illustrated in FIG. 9, the notch 1358 provides an oblique opening to the lumen 1360 of the cannula 1350. As best illustrated in FIG. 10, a partial circumferential wall 1362 of the cannula 1350 exists in the notch 1358, which a full circumferential wall 1364 of the cannula 1350 exists in the portion of the cannula 1350 disposed axially inward from the notch 1358. Also, as best illustrated in FIG. 9, the notch 1358 defines a distal tip 1366 suitable for forming an initial puncture opening in tissue during an implantation procedure.

Figure 12:
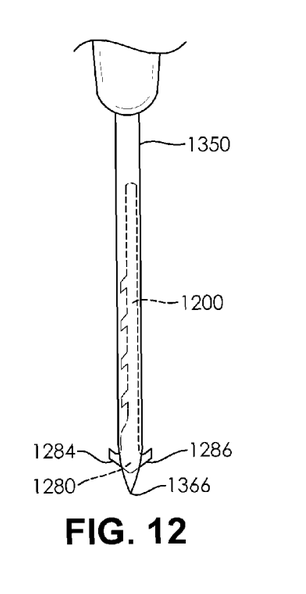
FIG. 12 is a partial top view of the delivery device illustrated in FIG. 9. A tissue adjustment implant is loaded in the cannula of the delivery device.

FIG. 12 illustrates the cannula 1350 of delivery device 1300 and the tissue adjustment implant 1200 of FIG. 6 disposed within the lumen 1360 of the cannula 1350. As illustrated in the figure, the tissue adjustment implant 1200 is positioned within the cannula 1350 such that the terminal point 1282 of the arrowhead 1280 of the tissue adjustment implant 1200 is disposed within the notch and axially inward from the distal tip 1366 of the cannula 1350. A portion of each of the sides 1284, 1286 of the arrowhead 1280 of the tissue adjustment implant extend laterally outward from the cannula 1350. With this configuration, the tissue adjustment implant can be implanted by pushing the cannula 1350, by applying force to the handle of the delivery device, for example, such that the distal tip 1366 punctures the tissue into which the tissue adjustment implant is to be implanted. By continuing to apply force in this manner, the portions of the sides 1284, 1286 of the arrowhead are forced into the tunnel formed by the cannula 1350. Once the tissue adjustment implant 1200 has been advanced into the tissue to a desirable or suitable distance, the cannula 1350 can be retracted by applying a reverse force on the handle of the delivery device. As this is performed, the sides 1284, 1286 of the arrowhead will engage the tissue and anchor the tissue adjustment implant 1200 in place, allowing the cannula 1350, and the delivery device, to be retracted while leaving the tissue adjustment implant in place.

The tissue adjustment implants can be formed of any suitable material or materials, and a skilled artisan will be able to select an appropriate material or materials for a tissue adjustment implant according to a particular embodiment based on various considerations, including the tissue with which the tissue adjustment implant is intended to be used, the technique by which the tissue adjustment implant will be implanted, and other considerations. Both synthetic and natural materials are considered suitable. Examples of suitable synthetic materials include polymeric materials, such as polyethylene, polypropylene and other flexible polymeric materials. Examples of suitable natural materials include tissue and tissue-derived materials. The inventors have determined that tissue adjustment implants formed of bioremodelable materials are particularly well-suited for implantation within and adjustment of various tissues in human and other animals at least because of the ability of such materials to remodel and become incorporated into adjacent tissues over time. These materials can provide a scaffold onto which cellular in-growth can occur, eventually allowing the material to remodel into a structure of host cells, which aids in the effectiveness of the tissue adjustment implant as a long-term support of the tissue being secured.

Particular advantage can be provided by tissue adjustment implants that incorporate a remodelable collagenous material. Such remodelable collagenous materials, whether reconstituted or naturally-derived, can be provided, for example, by collagenous materials isolated from a warm-blooded vertebrate, especially a mammal. Such isolated collagenous material can be processed so as to have remodelable, angiogenic properties and promote cellular invasion and ingrowth. Remodelable materials may be used in this context to stimulate ingrowth of adjacent tissues into an implanted construct such that the remodelable material gradually breaks down and becomes replaced by new patient tissue so as to generate a new, remodeled tissue structure. Such materials are considered suitable for use in the main body, projections, and plug portions of tissue adjustment implants.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the tissue adjustment implants, and their isolation and treatment, reference can be made, for example, to U.S. Pat. Nos. 4,902,508, 5,554,389, 5,993,844, 6,206,931, and 6,099,567.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when a tissue adjustment implant incorporates this sort of material, cells will invade the remodelable material upon implantation eventually leading to the generation of a newly-remodeled, functional tissue structure.

Submucosa-containing or other ECM tissue used in the tissue adjustment implants is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the inventive tissue adjustment implants.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source. In a dry state, a typical layer thickness for an as-isolated submucosa or other ECM tissue layer used in the invention ranges from about 30 to about 160 microns when fully dry, more typically from about 30 to about 130 microns when fully dry.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials used in a tissue adjustment implant can be derived from any suitable organ or other tissue source, usually sources containing connective tissues. The ECM materials processed for use in the inventive tissue adjustment implants will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the inventive tissue adjustment implants may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material used in an inventive tissue adjustment implant. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogeneic relative to the ECM material) or may be from a different species from the ECM material source (xenogeneic relative to the ECM material). In certain embodiments, ECM material will be xenogeneic relative to the patient receiving the graft, and any added exogenous material(s) will be from the same species (e.g. autologous or allogeneic) as the patient receiving the graft. Illustratively, human patients may be treated with xenogeneic ECM materials (e.g. porcine-, bovine- or ovine-derived) that have been modified with exogenous human material(s) as described herein, those exogenous materials being naturally derived and/or recombinantly produced.

The inventors have determined that SIS is particularly well-suited for use in the tissue adjustment implant devices described herein at least because of its well-characterized nature and ready availability. Furthermore, the inventors have determined that vacuum-pressed SIS provides a particularly advantageous material from which to form tissue adjustment implant devices that include one or more pluralities of projections, such as the tissue adjustment implants described and illustrated herein. Lyophilized SIS can also be used, and may be advantageous for tissue adjustment implants in which a relatively quicker remodeling time is desired. Radiopaque SIS can also be used, and may be advantageous for tissue adjustment implants for which enhanced visualization characteristics are desired.

The inventors have determined that a tissue adjustment implant having a main body formed of multiple layers laminated together provides a particularly advantageous structure. Thus, the main body can comprise a multilaminate construct. In these embodiments, any suitable number of layers can be used, and a skilled artisan will be able to select an appropriate number of layers for a particular tissue adjustment implant based on various considerations, including the intended use of the tissue adjustment implant and nature of the tissue intended to be supported by the tissue adjustment implant. The inventors have determined that a tissue adjustment implant having a main body formed of between 4 and 12 layers of an ECM material, such as SIS, provides a particularly advantageous structure for tissue adjustment implants intended for use in supporting the soft palate of a patient, such as in methods of treating Obstructive Sleep Apnea (OSA). A main body formed of between 6 and 10 layers of an ECM material, such as SIS, is also considered particularly advantageous. A main body formed of 8 layers of an ECM material, such as SIS, is also considered particularly advantageous. A main body formed of up to 60 layers of an ECM material, such as SIS, is also considered particularly advantageous. In these embodiments, the layers can be assembled together in any suitable manner and using any suitable technique or process. For multilaminate SIS constructs, the inventors have determined that vacuum-pressing of multiple layers of SIS provides a suitable laminate structure for use as a tissue adjustment implant as described herein. The layers in the multilaminate construct can be vacuum-pressed prior to assembly into the multilaminate construct. Alternatively, the multilaminate construct can be vacuum-pressed after assembly of the layers. Also alternatively, the layers can be vacuum-pressed prior to assembly and the assembly can be vacuum-pressed after assembly. The inventors have determined that use of vacuum-pressed SIS provides desirable durability and profile characteristics. When using a vacuum-pressed layers of an ECM material, such as SIS, any suitable number of vacuum-pressed layers can be used. The inventors have determined that a tissue adjustment implant having a main body formed of between 4 and 60 layers provides a particularly advantageous structure for tissue adjustment implants intended for use in supporting the soft palate of a patient, such as in methods of treating OSA. A main body formed of between 10 and 50 layers is also considered particularly advantageous. A main body formed of between 20 and 40 layers is also considered particularly advantageous. A main body formed of between 25 and 35 layers is also considered particularly advantageous. A main body formed of about 30 layers is also considered particularly advantageous. The inventors have determined that a tissue adjustment implant comprising a multilaminate construct comprised of 30 layers of vacuum-pressed SIS provides a suitable structure for use in methods of treating OSA.

The inventors have determined that a hybrid structure may provide a desirable balance between desired overall rigidity for the tissue adjustment implant and relative remodeling time. In this embodiment, a middle portion of the tissue adjustment implant is formed of lyophilized SIS, which provides a relatively quicker remodeling time, and the perimeter sections, including the ribbed portions, are formed of vacuum-pressed SIS, which provides a relatively high degree of overall rigidity. The middle portion in this embodiment is expected to remodel relatively quickly following implantation, enhancing the securement of the tissue adjustment implant. An opposite structure is also considered suitable and may be advantageous in certain circumstances.

A hybrid structure in which a mesh is embedded inside an SIS or other composition or between layers of SIS or of other material is also considered suitable. For example, a polymeric mesh, such as a mesh formed of polypropylene, can be disposed between layers of SIS during formation of the tissue adjustment implant. In these embodiments, the polymeric mesh will remain in the body following completion of remodeling by the SIS, which may enhance the overall anchoring of the supported tissue over time. A bioabsorable mesh, such as a mesh formed of polyglycolic acid or other bioabsorbable material, can also be included in the tissue adjustment implant in this manner and may be advantageous where supplemental support is desired that lasts beyond the remodeling time for the SIS, but that does not have the permanency associated with a polypropylene or other polymeric mesh. Examples of suitable structural arrangements of polymer and remodelable layers can be found in United States Patent Application Publication No. 2011/0166673 to Patel et al., for QUILTED IMPLANTABLE GRAFT, the entire contents of which are hereby incorporated into this disclosure.

A tissue adjustment implant, or portions thereof, can also be coated with particular materials to provide a desired property or properties. For example, the inventors have determined that coating a tissue adjustment implant with poly(lactic-co-glycolic acid) (PLGA) provides a desirable stiffening effect to the implant while also providing an agent that promotes an inflammatory response in tissue within which the tissue adjustment implant has been placed. In tissue adjustment implants that comprise a multilaminate construct, as describe above, a coating can be applied between layers during fabrication. For example, PLGA can be applied to or embedded within one, two, a plurality of, or all of the layers when making a main body that comprise a multilaminate construct.

The tissue adjustment implants are implanted by forming an opening in a target tissue, passing the first end of the tissue adjustment implant through the opening and into the tissue until the plug contacts the tissue surrounding the opening. If desired, additional pulling force can be applied to the first end to lift or otherwise adjust the position of the tissue through interaction with the plug. Once a desired position is achieved, a portion of the tissue adjustment implant, such as a portion near the first end of the tissue adjustment implant, can be sutured to the tissue. This is beneficial for maintaining the adjusted position of the tissue.

After passing the first end of the tissue adjustment implant through the opening in the tissue and into the tissue, the first end of the tissue adjustment implant, or a lead attached to it, can be manipulated to exit the tissue, either through an existing opening or by forming an opening, at a point at a distance from the opening through with the tissue adjustment implant entered the tissue. This is particularly advantageous for tissue adjustment implants that include a lead, such as a needle and suture attached to a first end of the tissue adjustment implant. Also, if desired, the tissue adjustment implant can be trimmed of excess main body such that the remainder of the tissue adjustment implant is flush or substantially flush with the opening through which the tissue adjustment implant exits the tissue. If this is performed, it is advantageously performed after the tissue adjustment implant is secured to the tissue, if performed, such that any desired adjusted position of the tissue is maintained after the trimming is completed.

Figure 5:
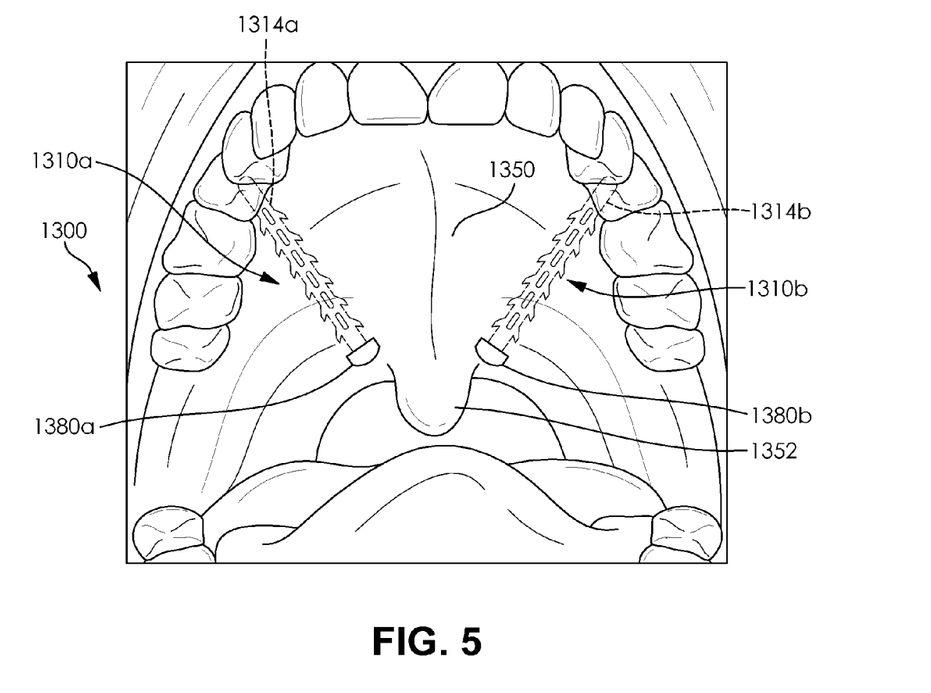
FIG. 5 is a schematic of an oral cavity of a patient within which two tissue adjustment implants have been placed.

The tissue adjustment implants are particularly well-suited for adjusting the position of the soft palate of a patient, such as a human being. Such an adjustment may be beneficial in the treatment of Obstructive Sleep Apnea (OSA). FIG. 5 illustrates a schematic of an oral cavity 1300 of a patient within which first 1310a and second 1310b tissue adjustment implants have been placed. In this example, each of the tissue adjustment implants 1310a, 1310b comprises a tissue adjustment implant according to the embodiment illustrated in FIGS. 2 and 2A. The first tissue adjustment implant 1310a has been implanted in the soft palate 1350 on a first side of the uvula 1352 and the second tissue adjustment implant 1310b has been implanted in the soft palate 1350 on a second, opposite side of the uvula 1352. Each tissue adjustment implant 1310a, 1310b has been implanted as described above, such that the respective plugs 1380a, 1380b have been buried just beneath the surface of the tissue of the soft palate 1350. Each tissue adjustment implant 1301a, 1301b was pulled taught after the respective plugs 1310a, 1310b had reached that position to achieve a desired lifting of the rear portion 1352 of the soft palate. Subsequently, the leads (not illustrated in FIG. 5)

were cut and removed from the tissue adjustment implants and the respective first ends 1314a, 1314b of the tissue adjustment implants 1310a, 1310b were sutured to the tissue of the soft palate 1350 to maintain the adjusted position of the soft palate 1350. In FIG. 5, the tissue adjustment implants 1310a, 1310b, were implanted by passing the tissue adjustment implants 1310a, 1310b through an opening made in the tissue toward the rear of the oral cavity 1300 and advancing them toward the front of the oral cavity 1300. While another approach can be used, this approach is suitable for tissue adjustment implants having a plug on their distal end, such as tissue adjustment implants 1310a, 1310b.

Figure 13:
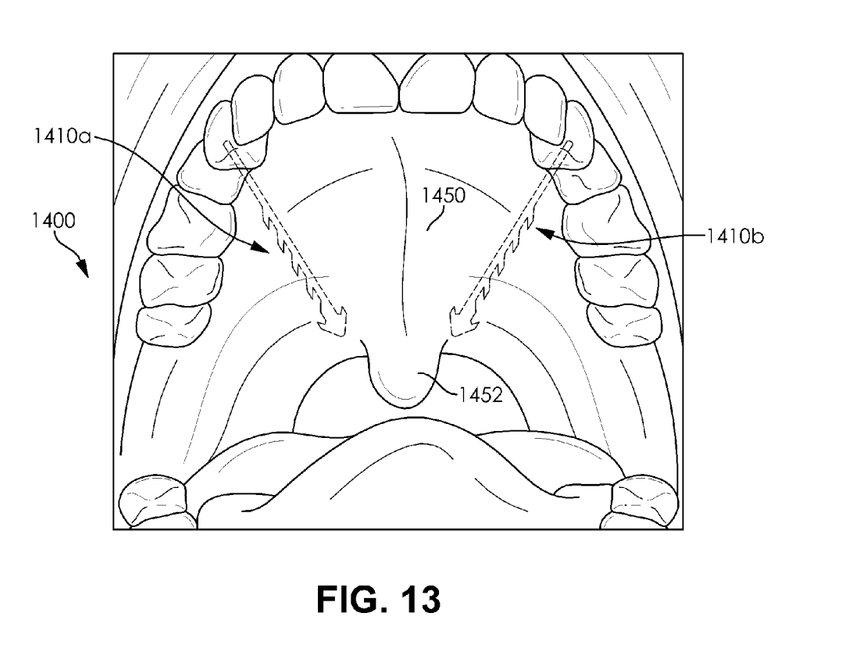
FIG. 13 is a schematic of an oral cavity of a patient within which two tissue adjustment implants have been placed.

FIG. 13 illustrates another schematic of an oral cavity 1400 of a patient within which first 1410a and second 1410b tissue adjustment implants have been placed. In this example, each of the tissue adjustment implants 1410a, 1410b comprises a tissue adjustment implant according to the embodiment illustrated in FIGS. 6, 6A and 6B. The first tissue adjustment implant 1410a has been implanted in the soft palate 1450 on a first side of the uvula 1452 and the second tissue adjustment implant 1410b has been implanted in the soft palate 1450 on a second, opposite side of the uvula 1452. Each tissue adjustment implant 1410a, 1410b has been implanted as described above with respect to the delivery device illustrated in FIGS. 8 through 12. In FIG. 13, the tissue adjustment implants 1410a, 1410b, were implanted by passing the tissue adjustment implants 1410a, 1410b through an opening made in the tissue toward the front of the oral cavity 1400 and advancing them toward the rear of the oral cavity 1400. While another approach can be used, this approach is suitable for tissue adjustment implants that lack a plug on their distal end and/or that have an anchor portion, such as the arrowhead on each of tissue adjustment implants 1410a, 1410b, on their proximal end, such as tissue adjustment implants 1410a, 1410b.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. A tissue adjustment implant comprising:
   a main body extending along a lengthwise axis and having first and second opposing ends, a longitudinal midpoint, first and second opposing sides, first and second opposing surfaces, and a first width extending from the first side to the second side orthogonally to the longitudinal axis and through the longitudinal midpoint;
   a first anchor portion disposed on the first end, the first anchor portion having a second width extending orthogonally to the longitudinal axis, the second width being greater than the first width; and
   a series of projections disposed on the first side, each projection of the series of projections extending away from the second end and the longitudinal axis of the main body;
   further comprising a throat portion that extends from the main body to the first anchor portion and transitions from the first width to the second width.

2. The tissue adjustment implant of claim 1, wherein the second side contains no projections.

3. The tissue adjustment implant of claim 1, wherein the first anchor portion defines an arrowhead having a first arrowhead side oriented at an angle to a second arrowhead side.

4. The tissue adjustment implant of claim 3, wherein the angle is an acute angle.

5. The tissue adjustment implant of claim 4, wherein the acute angle comprises an angle between about 35 degrees and about 90 degrees.

6. The tissue adjustment implant of claim 4, wherein the acute angle comprises an angle of about 45 degrees.

7. The tissue adjustment implant of claim 4, wherein the acute angle comprises an angle of 45 degrees.

8. The tissue adjustment implant of claim 3, wherein the angle is an obtuse angle.

9. The tissue adjustment implant of claim 3, wherein the angle is a right angle.

10. The tissue adjustment implant of claim 3, wherein the arrowhead defines a terminal point; and
    wherein the terminal point comprises a rounded point.

11. The tissue adjustment implant of claim 1, wherein at least one projection of the series of projections comprises a wing-shaped member having a base and an end, the base having a base width that extends parallel to the longitudinal axis of the main body and the end having an end width that extends parallel to the longitudinal axis of the main body; and
    wherein the base width is greater than the end width.

12. The tissue adjustment implant of claim 1, wherein each projection of the series of projections comprises a wing-shaped member having a base and an end, the base having a base width that extends parallel to the longitudinal axis of the main body and the end having an end width that extends parallel to the longitudinal axis of the main body and that is less than the base width.

13. The tissue adjustment implant of claim 1, wherein said tissue adjustment implant comprises a bioremodelable material.

14. The tissue adjustment implant of claim 13, wherein the bioremodelable material comprises an extracellular matrix (ECM) material.

15. The tissue adjustment implant of claim 14, wherein the extracellular matrix material comprises small intestine submucosa (SIS).

16. The tissue adjustment implant of claim 1, wherein said tissue adjustment implant comprises an integral, multi-laminate construct comprising layers of small intestine submucosa (SIS).

17. The tissue adjustment implant of claim 1, wherein the throat portion is only on the first side.

18. The tissue adjustment implant of claim 17, wherein the second side contains no projections.

19. The tissue adjustment implant of claim 1, wherein the main body, the first anchor portion, the series of projections, and the throat portion is formed as an integral unit.

20. A tissue adjustment implant comprising:
    a main body extending along a lengthwise axis and having first and second opposing ends, a longitudinal midpoint, first and second opposing sides, first and second opposing surfaces, and a first width extending from the first side to the second side orthogonally to the longitudinal axis and through the longitudinal midpoint;
    a first anchor portion disposed on the first end, the first anchor portion defining an arrowhead having a first arrowhead side oriented at an acute angle to a second arrowhead side and having a second width extending orthogonally to the longitudinal axis;

a throat portion that extends from the main body to the first anchor portion and transitions from the first width to the second width; and a series of projections disposed only on the first side, each projection of the series of projections extending away from the second end and the longitudinal axis of the main body and comprising a wing-shaped member having a base and an end, the base having a base width that extends parallel to the longitudinal axis of the main body and the end having an end width that extends parallel to the longitudinal axis of the main body and that is less than the base width.

* * * * *